United States Patent [19]
Checchi

[11] Patent Number: 5,607,689
[45] Date of Patent: Mar. 4, 1997

[54] LATEX ELEMENT DESIGNED TO ACHIEVE GUIDED TISSUE REGENERATION IN PERIODONTAL DENTAL THERAPY

[75] Inventor: Luigi Checchi, Bologna, Italy

[73] Assignee: I Sugheri s.r.l., Bologna, Italy

[21] Appl. No.: 582,014

[22] Filed: Dec. 28, 1995

Related U.S. Application Data

[63] Continuation of Ser. No. 199,820, Feb. 22, 1994, abandoned.

[30] Foreign Application Priority Data

Feb. 22, 1993 [IT] Italy .................. BO93A0059

[51] Int. Cl.[6] .................. A61C 5/00; A61C 5/14
[52] U.S. Cl. .................. 424/435; 433/136; 433/173; 433/175; 433/215; 600/37; 623/11; 623/16
[58] Field of Search .................. 433/136, 215, 433/173, 175; 424/435; 600/37; 623/11, 16

[56] References Cited

U.S. PATENT DOCUMENTS

| | | | |
|---|---|---|---|
| 300,600 | 6/1884 | Halsey | 433/136 |
| 300,660 | 6/1884 | Halsey | 433/215 |
| 1,579,608 | 7/1924 | Haudenshield | 433/136 |
| 4,721,465 | 1/1988 | Barasz | 433/137 |
| 4,828,491 | 5/1989 | Gray | 433/136 |
| 5,032,445 | 7/1991 | Scantlebury et al. | 428/158 |
| 5,068,107 | 11/1991 | Hollibush et al. | 424/435 |
| 5,197,882 | 3/1993 | Jernberg | 433/215 |
| 5,250,584 | 10/1993 | Ikada et al. | 523/114 |
| 5,360,341 | 11/1994 | Abramowitz | 433/215 |

*Primary Examiner*—Frederick Krass
*Attorney, Agent, or Firm*—Richard M. Goldberg

[57] ABSTRACT

An element designed to achieve tissue regeneration in periodontal dental therapy, comprising a membrane insertable under the gingiva and made from a non-resorbable, biologically acceptable, non-porous elastomer material having a thickness in the range of approximately 0.1 mm to 0.3 mm, the membrane being preformed according to pre-established shapes which depend on tooth size and shape, the membrane having at least one hole, each hole having a diameter smaller than that of a tooth to be treated.

10 Claims, 2 Drawing Sheets

LATEX ELEMENT DESIGNED TO ACHIEVE GUIDED TISSUE REGENERATION IN PERIODONTAL DENTAL THERAPY

This application is a continuation, of application Ser. No. 08/199,820 filed Feb. 22, 1994, now abandoned.

The object of this invention is an element designed to achieve the managed regeneration of tissue in dental therapy, and particularly lesions caused by periodontal diseases. This element consists of a membrane in latex or elastomer material that is inserted between the surgical flap on one side and the bone and radicular surface on the other.

SUMMARY OF THE INVENTION

This invention refers to an element designed to promote the regeneration of the connective tissue, the bone and the connective attachment of a diseased dental root by means of a membrane/barrier inserted between the flap and the tooth/bone.

It is known that in "pyorrhoea" there is a predominantly inflammatory process of the tissue of the parodontium, namely the gingiva, the periodontal ligament, the alveolar bone and the cement, the main symptom of which is the apical migration of the attachment with the formation of a pocket determined by detachment of the gums and bone destruction.

These phlogistic signs are accompanied by processes of tissue degeneration and destruction with re-absorption of the alveolar walls and degeneration of the surrounding tissue. This pathological process leads to the loss of the teeth.

The systems for treating this disease vary according to the stage of the disease itself.

At the present time, the most widely used, advanced stage method is a surgical one which entails the introduction of membranes between the surgical flap on one side and the bone and radical surface on the other side, so as to promote the managed regeneration of the diseased tissue.

The purpose of this invention is to obtain regeneration of these tissues allowing particular cell lines to be selectively chosen from the periodontal ligament and isolated in a manner that allow selective colonization of the root surface. This can be obtained by stopping the apical migration of the epithelium along the radicular surface and to stabilise the concealment formed in the earliest phase of healing of the wound. This is important because it protects the neoformed collagen fibres from possible breakage and at the same time forms a covering to promote the growth of the cells of the periodontal ligament and the growth of blood vessels from the base of the lesion.

Whether they are resorbable or otherwise, the membranes used have disadvantages which depend mainly on the type of material from which they are made. For example: non-resorbable membranes allow a greater degree of bone regeneration but they cause inflammation of the surrounding connective tissue and a second surgical operation is required to remove them.

By contrast, resorbable membranes, for which only one surgical operation is required, have a lower degree of regeneration than the other type.

In addition, both types of membrane are still relatively expensive and do not succeed in hermetically excluding the dental element from the surrounding tissue.

The aim of this invention is to allow the creation of an element for the regeneration of tissue, particularly in periodontal diseases.

This element consists of a membrane made from latex or another elastomer material, such as synthetic polymers, polyurethane, SBS, SEBS and even from synthetic latex such as neoprene or nitrile; the material must however be nonresorbable and have a thickness of between 0.1 and 0.3 mm so as to achieve maximum elasticity. This membrane permits the complete covering of the root on both sides (or from one single side) in order to:

a) protect and promote stable congealment on all sides of the tooth;

b) form an insurmountable barrier to the passage of germs and/or bacteria present in the oral cavity and thus prevent the possibility of infection;

c) exclude lines of cells such as the epithelial cells;

d) allow wound stabilization (clot adhesion+clot stability).

Recent studies have in fact suggested that the regeneration of the tissue can be managed by allowing particular lines of cells to be isolated so as to permit the selective colonisation of the surface to the root, preventing the apical migration of the epithelium and enabling the wound to stabilise during healing.

Thanks to the barrier created by the membrane, the bone, the parodontal ligament, the cement and the connective tissue, which are slower-growing, can reform and recreate a normal and ideal dental anatomy.

BRIEF DESCRIPTION OF THE DRAWINGS

With reference to the attached drawings which illustrate in schematic form an example of how the invention can be realised.

The membrane (1), through a small hole whose diameter is smaller than that of the tooth (2), is made to slide on the tooth so as to cover it completely on both sides. During the surgical operation the roots are planed and scaled using manual and ultrasonic instruments and conditioned with ortophosforic acid.

Figure 1:
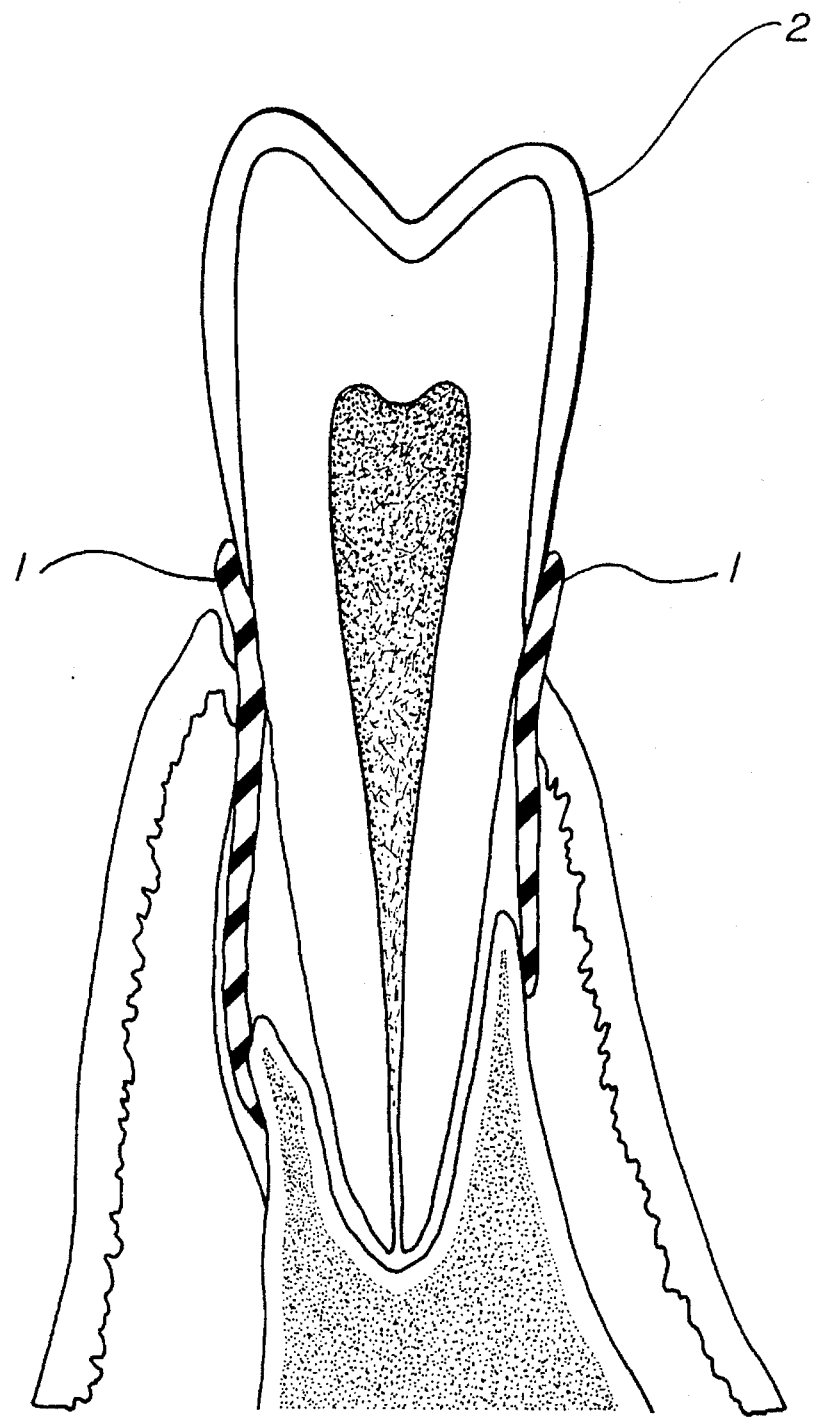
FIG. 1 shows the positioning of the membrane around the tooth.
Figure 2D:
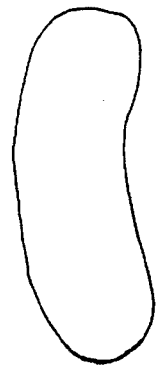
FIGS. 2A–2D show the possible configurations of the membrane.
Figure 2C:
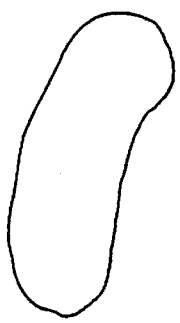
Figure 2B:
Figure 2A:
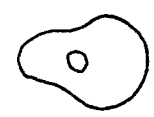

The membrane, pre-shaped as shown in FIG. 2, which has previously been sterilised, is adapted to one or more teeth at the desired height. Visually it resembles a tent in shape. The edges are then re-adjusted on the outer surface of the membrane and secured with a suture below the flaps. In FIGS. 2A–2D the membrane (1) is shaped according to requirements, as in FIG. 2A: for a single tooth; in FIG. 2B: right-side sextant; in FIG. 2C: left-side sextant; and in FIG. 2D: front, top or bottom for a single buccal or lingual defect.

When the suture is removed, the operation area in patients in whom the membrane has been inserted may show a contraction of the edge of the primary margin and the surgically introduced membrane may emerge under the edges. This membrane permits a new attachment (of the periodontal ligament), new cement, and new bone filling of the bone loss, re-establishing normal or fairly normal anatomical conditions.

The membrane as described above also has the advantage of being inexpensive.

Films of substances known as "grow factors" or regenerative substances can be set in contact with the membrane to further stimulate fibroblast regeneration.

By virtue of its characteristics, the membrane forming the object of this invention may also be used in implantation techniques.

I claim:

1. A method for achieving tissue regeneration in periodontal dental therapy, comprising the steps of:

inserting a membrane made only from a non-resorbable, biologically acceptable, non-porous elastomer latex material having at least one hole with a diameter smaller than that of a tooth, over said tooth such that the tooth extends through said hole and said membrane entirely surrounds the tooth by 360°;

inserting ends of said membrane under the gingiva so as to form an insurmountable barrier to the passage of microorganisms present in the oral cavity; and leaving said membrane under the gingiva and around the tooth for a time sufficient for healing to occur.

2. A method according to claim 1, wherein said latex material is a natural latex material.

3. A method according to claim 1, wherein said latex material is a synthetic latex material.

4. A method according to claim 3, wherein said synthetic latex material is selected from the group consisting of neoprene and nitrile.

5. A method according to claim 1, wherein said membrane has a thickness in the range of approximately 0.1 mm to 0.3 mm.

6. A method according to claim 1, further comprising the steps of preforming said membrane according to pre-established shapes which depend on tooth size and shape, and shaping said membrane to cover opposite sides of the tooth at the same time.

7. A method according to claim 6, further comprising the step of shaping said membrane to cover single buccal lesions.

8. A method according to claim 6, further comprising the step of shaping said membrane to cover single lingual lesions.

9. A method according to claim 1, further comprising the steps of preforming said membrane according to pre-established shapes which depend on tooth size and shape, and shaping said membrane to cover single buccal lesions.

10. A method according to claim 1, further comprising the steps of preforming said membrane according to pre-established shapes which depend on tooth size and shape, and shaping said membrane to cover single lingual lesions.

* * * * *